(12) United States Patent  (10) Patent No.: US 9,199,049 B2
Attwood  (45) Date of Patent: Dec. 1, 2015

(54) EXPIRATORY VOLUME RESERVOIR FOR A VENTILATOR PATIENT CIRCUIT

(76) Inventor: Jeffrey A Attwood, Mooresville, IN (US)

( * ) Notice: Subject to any disclaimer, the term of this patent is extended or adjusted under 35 U.S.C. 154(b) by 1923 days.

(21) Appl. No.: 11/923,439

(22) Filed: Oct. 24, 2007

(65) Prior Publication Data

US 2009/0107499 A1  Apr. 30, 2009

(51) Int. Cl.
*A61M 16/00* (2006.01)
*A61M 16/08* (2006.01)
*A61M 16/04* (2006.01)

(52) U.S. Cl.
CPC ....... *A61M 16/0075* (2013.01); *A61M 16/0833* (2014.02); *A61M 16/0468* (2013.01); *A61M 2016/0036* (2013.01)

(58) Field of Classification Search
CPC .............. A61M 16/0075; A61M 16/0833; A61M 2016/0036; A61M 16/0468
USPC ............. 128/204.19, 204.21–204.29, 205.12, 128/204.18, 205.13, 205.14, 205.21, 128/207.14, 207.15, 207.16; 702/19, 31, 32
See application file for complete search history.

(56) References Cited

U.S. PATENT DOCUMENTS 7,913,690 B2 * 3/2011 Fisher et al. ............. 128/204.23

* cited by examiner

*Primary Examiner* — Victoria J Hicks
(74) *Attorney, Agent, or Firm* — Swanson & Bratschun, L.L.C.

(57) ABSTRACT

A ventilating system for providing inspiratory air to and receiving expiratory air from a patient in a respiratory cycle. A ventilator has an inspiratory outlet for providing inspiratory air and an expiratory inlet for receiving expiratory air. A patient circuit in fluid communication with the lungs of the patient conveys inspiratory air during the inspiratory phase and expiratory air during the expiratory phase. A flow transducer in fluid communication with the patient circuit detects a minimum volume of expiratory air in the patient circuit during the expiratory phase. An elastic reservoir in fluid communication with the patient circuit and the flow transducer expands to a first volume during the inspiratory contracts to a second volume during the expiratory phase. The volume difference between the first volume and the second volume is at least equal to the minimum volume threshold.

8 Claims, 5 Drawing Sheets

EXPIRATORY VOLUME RESERVOIR FOR A VENTILATOR PATIENT CIRCUIT

TECHNICAL FIELD

The invention is directed to ventilator patient circuits and more particularly to an expiratory volume reservoir for a ventilator patient circuit capable of diverting expiratory air to promote patient speech.

BACKGROUND

Medical ventilators have been used for a number of years to simulate a breathing cycle of patients unable to breathe on their own. In some instances ventilators provide temporary assist for defined periods, for example, when normal patient breathing is interrupted by a surgical procedure. In other instances, ventilator use can be much longer term. Particularly with long-term ventilator use, conventional patient circuits associated with the ventilator do not allow patients to produce an audible laryngeal voice. This is because typically the patient is coupled to the ventilator by a patient circuit including a cuffed tracheotomy tube inserted into the trachea of the wearer below the level of the vocal chords. The cuff on the tracheotomy tube is inflated, for example, with air, so that the cuff seals substantially fluid tight against the wall of the trachea. The effect of the cuff is to provide a closed mechanical respiratory system that completely bypasses the upper airway above the level of the tracheotomy tube, including the vocal chords. One result is the elimination of exhaled airflow up through the vocal chords.

To enable such patients to produce audible laryngeal voice, valved tracheotomy tubes have been developed. One example is a valved-fenestrated tracheotomy tube having an inner and outer cannulae described in Blom, U.S. Pat. No. 6,722,367, the contents of which are incorporated in their entirety herein. Such a valved tracheotomy tube can be used to divert expiratory air from a patient circuit associated with a ventilator up through the wearer's vocal chords, mouth and nose, permitting audible vocal chord vibrations for speech. The Blom valved tracheotomy tube has significantly improved the quality of life for many long-termed ventilated patients by enabling patient speech using their own vocal chords. However, one problem with the Blom device and any other system diverting expiratory air from a patient circuit is the volume of expiratory air in the patient circuit is greatly reduced if not eliminated. However, virtually all ventilators utilize flow transducers to continuously monitor the volume of expiratory air in the patient breathing circuit. If the transducer detects that the volume of expiratory air drops below a minimum volume threshold, an alarm is generated. The alarm is intended to warn an operator there is an inadequate supply of expiratory air in the system which could mean, among other things, a leak in the system. Thus, diverting expiratory air to promote patient speech can have the undesirable effect of generating an alarm signal indicating an inadequate volume of expiratory air. Due to the life critical nature of ventilators, the expiratory air volume detection system cannot simply be disabled.

The present invention is directed to overcoming one or more of the problems discussed above.

SUMMARY

A first aspect is a ventilation system providing inspiratory air to a patient and receiving expiratory air from the patient. The ventilation system comprises a ventilator operable between an inspiratory phase and an expiratory phase of a respiration cycle. The ventilator has an inspiratory outlet for providing inspiratory air to a patient during the inspiratory phase and an expiratory inlet for receiving expiratory air from the patient during the expiratory phase. A patient circuit is configured in fluid communication with the lungs of a patient. The patient circuit conveys inspiratory air from the inspiratory outlet to a patient's lungs during the inspiratory phase and conveys expiratory air from the patient's lungs to the expiratory inlet during the expiratory phase. A flow transducer is provided in fluid communication with the patient circuit. The flow transducer is configured to detect a minimum volume of expiratory air in the patient circuit during the expiratory phase of a respiratory cycle. An elastic reservoir is provided in fluid communication with the patient circuit and the flow transducer. The elastic reservoir is configured to expand to a first volume during the inspiratory phase of the respiratory cycle and contract to a second volume during the expiratory phase of the respiratory cycle. A volume difference between the first volume and the second volume is at least equal to the minimum volume. In this manner, the elastic reservoir provides the minimum volume of air to the flow transducer during an expiratory phase of a respiration cycle even if expiratory air from the patient is diverted out of the patient circuit. In one embodiment the elastic reservoir comprises an elastic enclosure and a fitting operatively associated with the elastic enclosure. The fitting is configured to allow connection between the patient circuit and the elastic enclosure. In such an embodiment the elastic enclosure may comprise an accordion sidewall. The elastic enclosure may also be integrally made of silicone.

A second aspect is a method for enabling a patient breathing with the aid of a ventilator to speak without triggering a low expiratory air volume alarm from the ventilator. The method comprises providing a ventilator operable between an inspiratory phase and an expiratory phase of a respiration cycle. The respirator has an inspiratory outlet for providing inspiratory air to a patient during the inspiratory phase and an expiratory outlet for receiving expiratory air from a patient during the expiratory phase. The ventilator further includes a flow transducer for determining a minimum volume of expiratory air during the expiratory phase of a respiration cycle. A patient circuit is attached in fluid communication with the lungs of a patient and further attached to the inspiratory outlet and expiratory inlet to convey inspiratory air from the inspiratory outlet to the patient's lung during the inspiratory phase and to convey expiratory air from the patient's lungs to the expiratory inlet during the expiratory phase. The method further includes diverting expiratory air from the patient circuit over the patient's vocal chords, mouth and nose permitting audible vocal chord vibrations for speech and providing a volume of air at least equal to the minimum volume to the transducer during the diverting step. The step of providing a volume of air may include providing an elastic reservoir in fluid communication with the patient circuit and the flow transducer. The elastic reservoir is configured to expand to a first volume during the inspiratory phase and contract to a second volume during the expiratory phase, with a volume difference between the first volume and the second volume being at least equal to the minimum volume.

Another aspect is a reservoir for use in a ventilator patient circuit wherein a ventilator provides air for inhalation to the patient circuit at a first pressure and enables patient exhalation by allowing the circuit pressure to drop to a second pressure less than the first pressure. The ventilator has a flow transducer for detecting a minimum volume of expiratory air an producing an alarm signal if the minimum volume of expiratory air is not detected. The reservoir comprises an elastic enclosure which attains a first volume when subjected to the first pressure and a second volume when subjected to the second pressure. The difference between the first volume and the second volume is a volume sufficient to prevent a flow transducer on an operatively associated ventilator from producing an alarm signal. A fitting is operatively associated with the elastic enclosure, the fitting being configured to allow connection between the elastic enclosure and a ventilator patient circuit. The reservoir may comprise the elastic enclosure having an accordion wall. Further, the elastic enclosure may be integrally made of silicone.

Yet another aspect is a ventilator patient circuit for use with a ventilator having a volumetric expiratory air volume detector operatively associated therewith, the ventilator further having an inspiratory outlet and an expiratory inlet. The ventilator cycles between an inspiratory phase and an expiratory phase of a breathing cycle. The ventilator patient circuit comprises a tube for conveying air between a ventilator inspiratory outlet, a patient and an expiratory inlet. An elastic reservoir is provided in fluid communication with the tube, the elastic reservoir being configured to expand to a first volume during an inspiratory cycle of a ventilator and to elastically contract to a second volume less than the first volume during an expiratory cycle of a ventilator. In this manner the elastic reservoir releases a volume of air to the tube during the expiratory cycle, the volume of air being sufficient to prevent the volumetric exhalation detector from giving a false alarm. The elastic reservoir may comprise an accordion sidewall. The elastic reservoir may be integrally made of silicone.

DETAILED DESCRIPTION OF THE EMBODIMENTS

Figure 1:
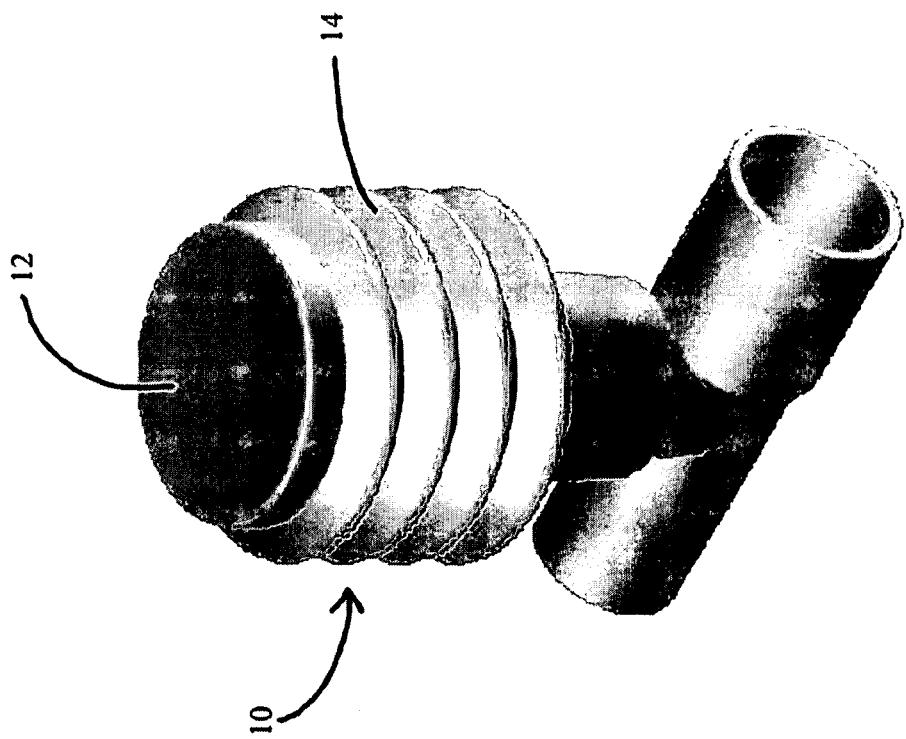
FIG. 1 is a perspective view of an expiratory volume reservoir attached to a "T" fitting.

FIG. 1 is a perspective view of an expiratory volume reservoir 10 for use in a ventilator patient circuit. The expiratory volume reservoir 10 consists of an elastic enclosure 12 which is configured to attain a first volume when subjected to a first pressure and a second volume when subject to a second pressure. The elastic enclosure 12 may have any configuration and be made of any material capable of attaining the first and second volumes when subjected to the first and second pressures. For example, in the embodiment illustrated in FIG. 1, the elastic enclosure comprises a bellows having an accordion sidewall 14. In this embodiment, the elastic enclosure 12 is integrally injection molded from silicone.

Figure 2:
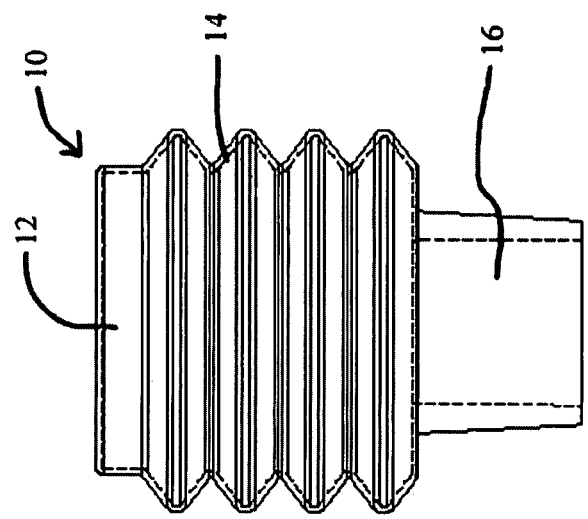
FIG. 2 is a side elevation view of the expiratory volume reservoir of FIG. 1.
Figure 4:
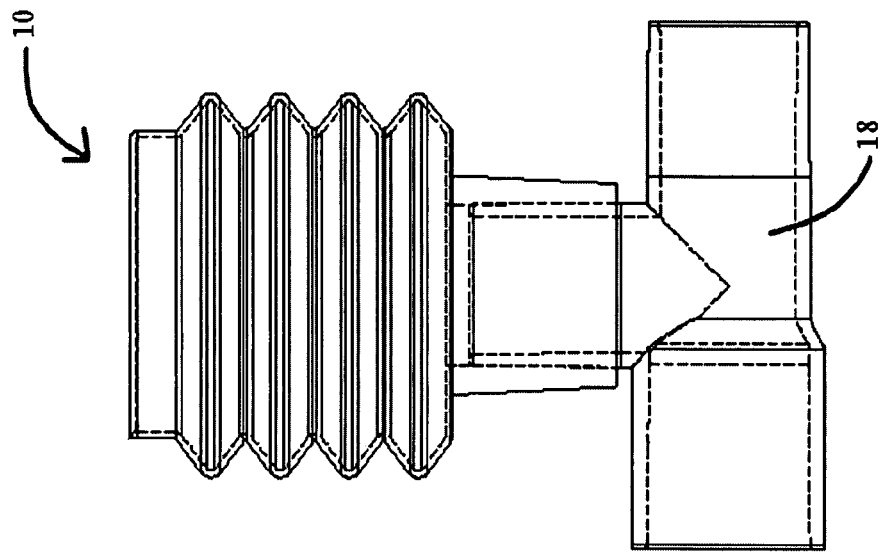
FIG. 4 is a side elevation view of the expiratory volume reservoir and "T" fitting of FIG. 1.
Figure 3:
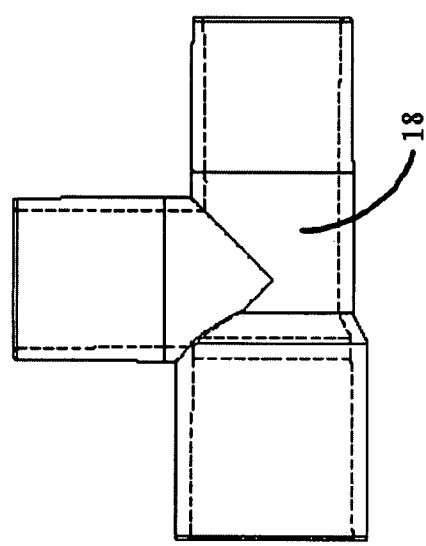
FIG. 3 is a side elevation view of the "T" fitting of FIG. 1.

Referring to FIG. 2, the elastic enclosure 12 further includes an integrally molded inlet fitting 16. The inlet fitting 16 is configured to be received on a T-fitting 18, illustrated in FIG. 3. Alternatively, the inlet fitting could be a separate piece adhered in any known manner such as an adhesive or heat staking to the elastic enclosure. The expiratory volume reservoir 10 is shown fitted on a T-fitting in FIG. 4. As understood of those skilled in the art of respiratory therapy, the T-fitting 18 may be a standard polypropylene, polycarbonate or other suitable resin compatible with known patient circuit tubing.

The volume difference between the first volume and the second volume must be a volume sufficient to prevent a flow transducer in an operatively associated ventilator from producing an alarm signal indicating low expiratory air volume. Typically, this volume is in the range of 30-50 mL, though other ranges of volumes may be required for atypical ventilators or future ventilators, which may require ranges of 20-100 mL, or even a greater range of volumes. The minimum volume necessary to prevent a low expiratory air volume may be adjustable and selectable by a user.

Figure 5:
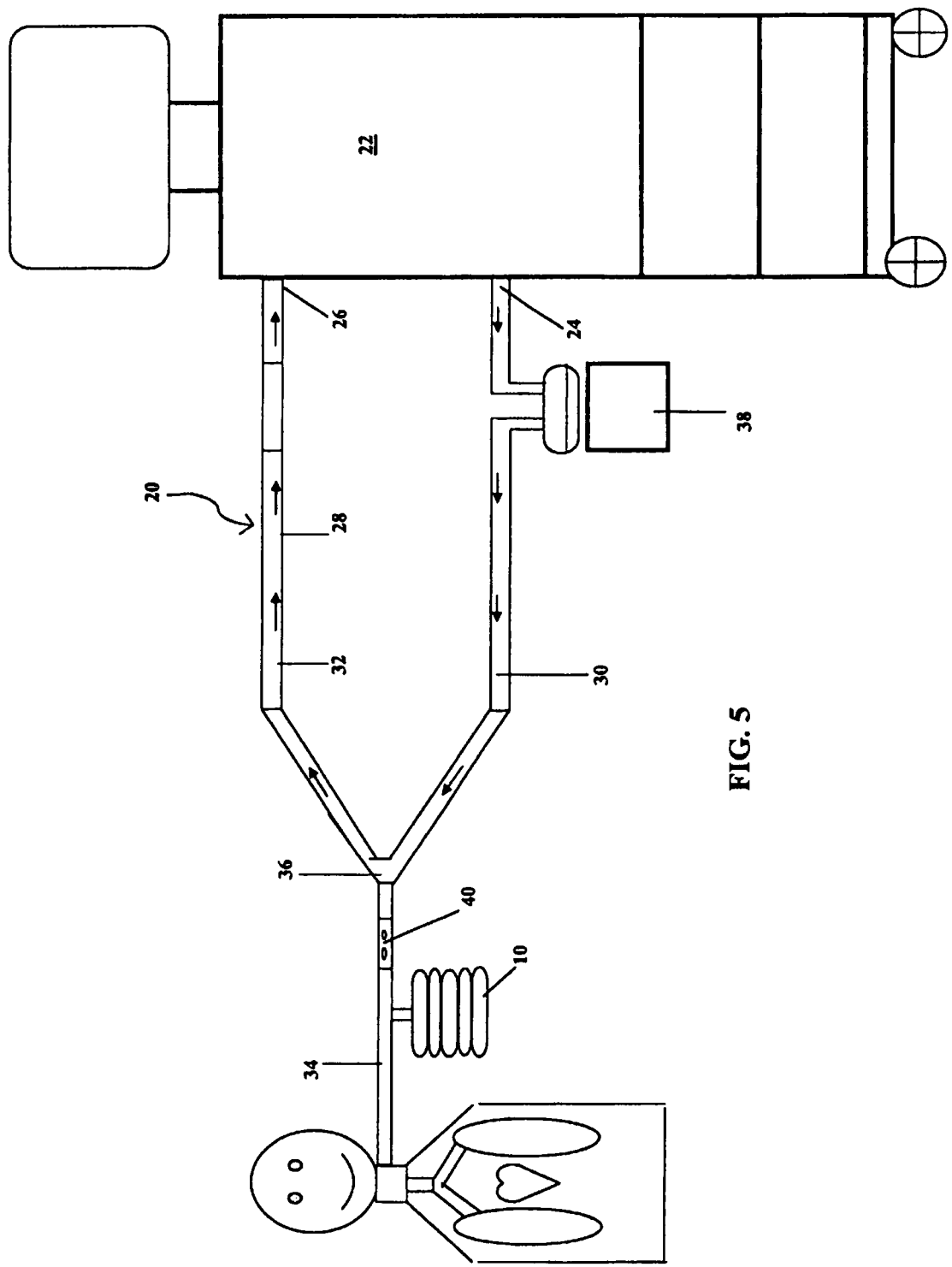
FIG. 5 is a schematic representation of a ventilator and patient circuit with an expiratory volume reservoir installed on a patient segment adjacent a proximal flow transducer.

FIG. 5 illustrates schematically an example of a patient circuit 20 and ventilator 22 with which the expiratory volume reservoir 10 can be used. As illustrated in FIG. 5, the ventilator 22 includes an inspiratory outlet 24 from which inspiratory air leaves the ventilator 22 and an expiratory inlet 26 through which expiratory air reenters the ventilator 22. As known in the art, the ventilator 22 includes mechanisms for circulating inspiratory air and expiratory air from a patient and various monitors, such as pressure monitors and expiratory volume monitors to ensure proper operation of the ventilator 22. In the patient circuit 20 illustrated in FIG. 5, the patient circuit 20 comprises a tube 28 extending between the inspiratory outlet 24 and the expiratory inlet 26. The tube 28 may include a number of tube segments such as an inspiratory segment 30 and an expiratory segment 32 and a patient connect segment 34 joined by a Y-fitting 36. In the embodiment illustrated in FIG. 5, a humidifier/heater 38 is provided in fluid communication with the inspiratory segment 30. A proximal flow transducer 40 is provided in fluid communication with the patient connect segment 34. The flow transducer 40 functions to detect a minimum volume of expiratory flow communicating therewith and produces an alarm signal which is relayed to the ventilator if the minimum expiratory volume is not detected. In many ventilator 22 systems, the minimum volume threshold is variable in accordance with user needs. With further reference to FIG. 5, an expiratory volume reservoir 10 is provided between the patient and the proximal flow transducer. As described above, the expiratory volume reservoir is expanded to a first volume when subjected to increased pressure during an inspiratory phase of a respiration cycle and decreases to a second volume when subjected to a decreased pressure during the expiratory phase of a respiratory cycle. Thus, during the expiratory phase the expiratory volume reservoir releases a volume of air which is detected by the volume flow transducer. This volume of air is greater than or equal to a minimum volume threshold being monitored by the flow transducer 40. In this manner the expiratory volume reservoir prevents the flow transducer from producing a low expiratory air volume warning if expiratory flow back to the expiratory inlet is diverted by the patient, for example by a patient using a Blom valved tracheotomy tube to divert air from the patient circuit over the patient's vocal chords, nose and mouth so as to speak.

Figure 6:
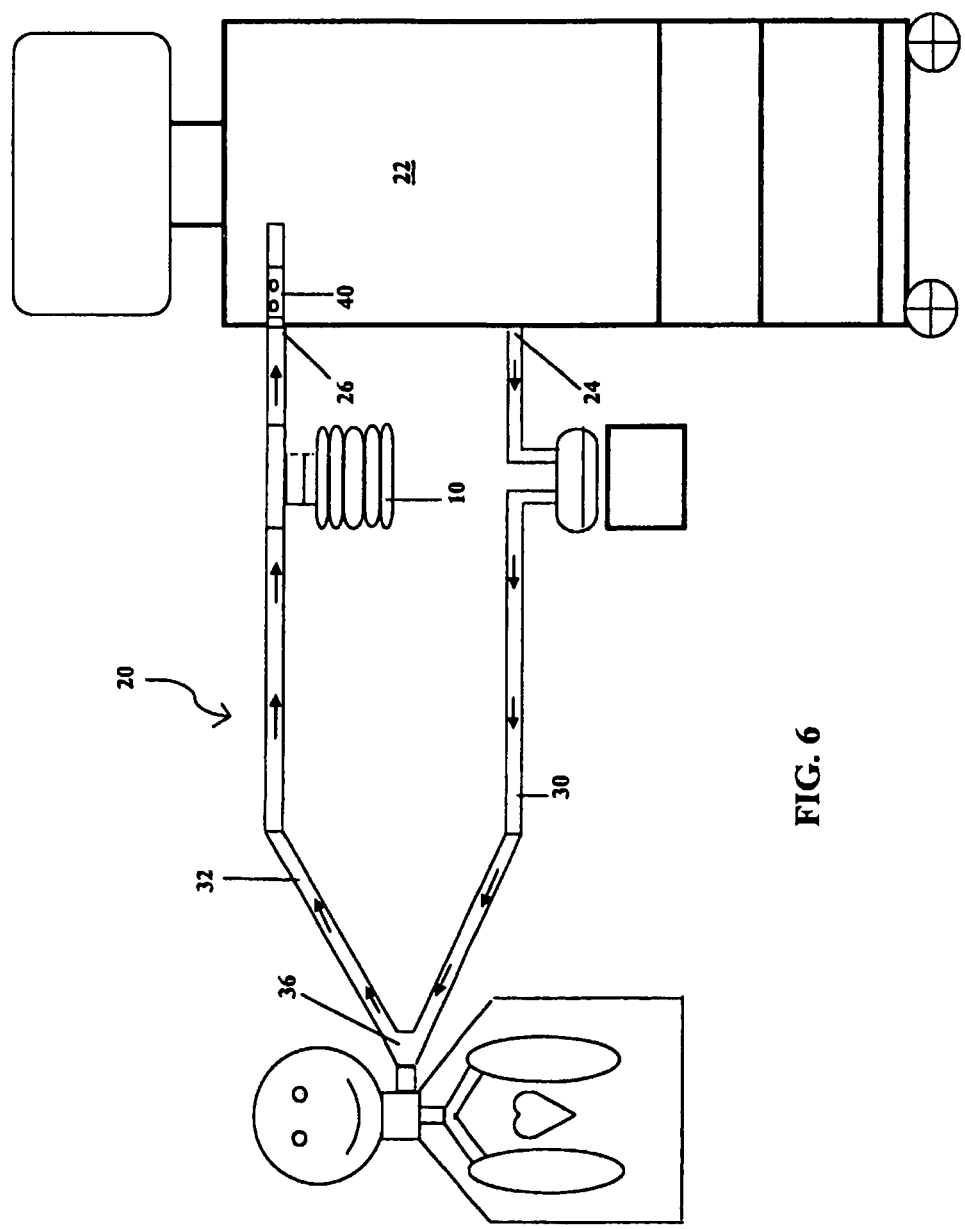
FIG. 6 is a schematic representation of a ventilator and patient circuit with the ventilator having a flow transducer downstream of the expiratory inlet an the expiratory volume reservoir located on the expiratory segment near the expiratory inlet.

FIG. 6 shows an alternate embodiment with the flow transducer 40 located within the expiratory inlet of the ventilator 22. In this embodiment the expiratory volume reservoir 10 would be located in the expiratory segment 32 in close proximity to the expiratory inlet 26 so as to provide a volume of air to the transducer 40 when the patient diverts air from the patient circuit 20.

Figure 7:
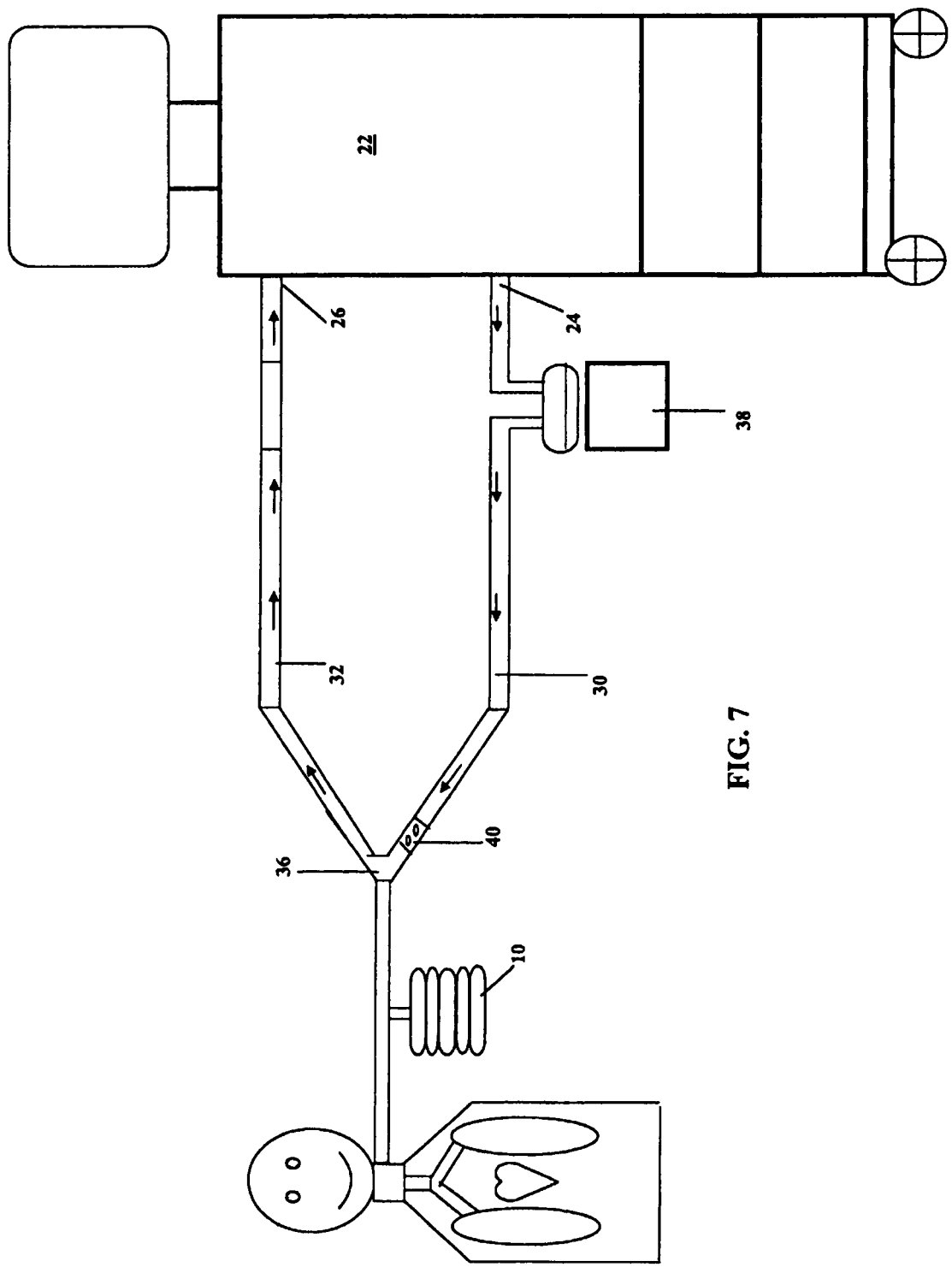
FIG. 7 is a schematic representation of a ventilator and patient circuit with the flow transducer in an expiratory segment near the Y-fitting and the expiratory volume reservoir located on the patient segment near the Y-fitting.

FIG. 7 is another embodiment of a ventilator where a flow transducer 40 is located in an inspiratory segment 30. In this embodiment the expiratory volume reservoir 10 is positioned in the patient segment which provides sufficient proximity for the volume of air to be delivered to the flow transducer 40.

The expiratory volume reservoir described herein can be used to prevent false low volume alarms during intentional diversion of expiratory air for patient speech with a wide variety of ventilators. Representative ventilators with which they expiratory volume reservoir can be used to prevent false expiratory volume alarms include: Viasys-Bear 1000/1000 T/ES, Viasys-Bird 8400ST/Sti; Viasys-Bird T-Bird AVS I, II, III, Viasys-Vela, Viasys-Avea, Viasys/Pulmonetic Systems LTV 900, 950, 1000 & 1200; Drager-Evita 4, XL; Drager-Evita 2 Dura & Savina, Hamilton-Amadeus FT; Hamilton-Velolar FT; Hamilton Galileo; Hamilton-Raphael; Puritan Bennett-740, 760, 840; Puritan Bennett-7200 Series, Puritan Bennett-Infrasonics Adult Star 1500/2000; Newport-Wave E200; Newport-E500; Newport-HT50; Siemens/Maquet-Servo 900C; Siemens/Maquet-Servo 300/300A, Siemens/Maquet-Servo-i; Respironics-PLV 100/102, Respironics-Esprit, eVent Medical-Inspiration, Versamed-iVent 201. These various ventilators may use proximal flow transducers, inspiratory flow transducer or flow transducers within the ventilator unit downstream of the expiratory outlet, and the position of the expiratory volume reservoir would be positioned accordingly with reference to FIGS. 5-7. The expiratory volume reservoir may also be used with any other device diverting expiratory air from a patient circuit of a ventilator.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

What is claimed is:

1. A ventilating system for providing inspiratory air to a patient and receiving expiratory air from the patient, the ventilation system comprising:

a ventilator operable between an inspiratory phase and an expiratory phase of a respiration cycle, the ventilator having an inspiratory outlet for providing inspiratory air to a patient during the inspiratory phase, an expiratory inlet for receiving expiratory air from a patient during the expiratory phase;

a patient circuit configured for fluid communication with the lungs of a patient for conveying inspiratory air from the inspiratory outlet to a patient's lungs during the inspiratory phase and for conveying expiratory air from the patient's lungs to the expiratory inlet during the expiratory phase;

a flow transducer in fluid communication with the patient circuit, the flow transducer being configured to detect a minimum volume of expiratory air in the patient circuit during the expiratory phase of a respiration cycle;

a diversion device for selectively diverting expiratory air from the patient circuit to enable patient speech during the expiratory phase; and an elastic reservoir comprising an elastic enclosure comprising an accordion side wall and a fitting operatively associated with the elastic enclosure, the fitting being configured to allow connection between the patient circuit and the elastic enclosure, the elastic enclosure being in fluid communication with the patient circuit and the flow transducer, the elastic reservoir being configured to expand to a first volume during the inspiratory phase of the respiratory cycle and contract to a second volume during the expiratory phase of the respiratory cycle, a volume difference between the first volume and the second volume being at least equal to the minimum volume of expiratory air, the elastic reservoir being configured to provide the volume difference of air to the flow transducer during an expiratory phase of a respiration cycle, wherein the flow transducer will detect the volume difference of air at least equal to the minimum volume of expiratory air even if expiratory air is diverted from the patient circuit by the diversion device to enable patient speech.

2. The ventilating system of claim 1 wherein the elastic enclosure is integrally made of silicone.

3. A method for enabling a patient breathing with the aid of a ventilator to speak without triggering a low expiratory volume of air alarm from the ventilator, the method comprising:

providing a ventilator operable between an inspiratory phase and an expiratory phase of a respiration cycle, the ventilator having an inspiratory outlet for providing inspiratory air to a patient during the inspiratory phase and an expiratory outlet for receiving expiratory air from a patient during the expiratory phase, the ventilator having a flow transducer operatively associated therewith for detecting a minimum volume of expiratory air during the expiratory phase of a respiration cycle;

attaching a patient circuit in fluid communication with the lungs of a patient conveying inspiratory air from the inspiratory outlet to the patient's lungs during the inspiratory phase and conveying expiratory air from the patient's lungs to the expiratory inlet during the expiratory phase;

diverting expiratory air from the patient circuit over the patient's vocal chords, mouth and nose permitting audible vocal chord vibrations for speech; and providing a minimum volume of air at least equal to the minimum volume of expiratory air to the transducer during the diverting step.

4. The method of claim 3 wherein the step of providing a minimum volume of air comprises providing an elastic reservoir in fluid communication with patient circuit and the flow transducer, the elastic reservoir being configured to expand to a first volume during the inspiratory phase and contract to a second volume during the expiratory phase, a volume difference between the first volume and the second volume being at least equal to the minimum volume.

5. A reservoir for use in a ventilator patient circuit, wherein a ventilator provides air for inhalation to a patient circuit at a first pressure and enables patient exhalation by allowing the circuit pressure to drop to a second pressure less than the first pressure, the ventilator having a flow transducer for detecting a minimum volume of expiratory air and producing an alarm signal if the minimum volume of expiratory air is not detected, the reservoir comprising:

an elastic enclosure comprising an accordion sidewall, the elastic enclosure attaining a first volume when subject to the first pressure and a second volume when subject to the second pressure, the difference between the first volume and the second volume being a volume sufficient to prevent a flow transducer on an operatively associated ventilator from producing an alarm signal; and a fitting operatively associated with the elastic enclosure, the fitting being configured to allow connection between the elastic enclosure and a ventilator patient circuit.

6. The reservoir of claim 5 further comprising the elastic enclosure being integrally made of silicone.

7. A ventilator patient circuit for use with a ventilator having a volumetric expiratory air detector operatively associated therewith to provide a signal if a minimum volume of expiratory air is not detected, the ventilator further having an inspiratory outlet and an expiratory inlet, the ventilator cycling between an inspiratory phase and an expiratory phase, the ventilator patient circuit comprising:
   a tube for conveying air between a ventilator inspiratory outlet, a patient and an expiratory inlet;
   a diversion device selectively diverting expiratory air from the tube during the expiratory phase to enable patient speech; and
an elastic reservoir comprising an accordion sidewall and being in fluid communication with the tube, the elastic reservoir being configured to expand to a first volume during an inspiratory cycle of a ventilator and to elastically contract to a second volume less than the first volume during an expiratory cycle of a ventilator to thereby release a volume of air to the tube during the expiratory cycle, the volume of air being sufficient to prevent the volumetric expiratory air detector from providing an alarm signal even if expiratory air is diverted from the patient circuit by the diversion device to enable speech.

8. The ventilator patient circuit of claim 7 further comprising the elastic reservoir being integrally made of silicone.

\* \* \* \* \*